United States Patent [19]

Schniewind

[11] 4,313,340
[45] Feb. 2, 1982

[54] DEVICE FOR MEASURING THE SOLIDS CONTENT OF A LIQUID

[75] Inventor: Manfred Schniewind, Essen, Fed. Rep. of Germany

[73] Assignee: Ihle Ingenieurgesellschaft mbH, Düsseldorf, Fed. Rep. of Germany

[21] Appl. No.: 119,956

[22] Filed: Feb. 8, 1980

[30] Foreign Application Priority Data

Mar. 31, 1979 [DE] Fed. Rep. of Germany ....... 2913058

[51] Int. Cl.³ ........................................... G01N 15/04
[52] U.S. Cl. .................................................. 73/61.4
[58] Field of Search ................. 73/61.4, 432 PS, 61 R

[56] References Cited

U.S. PATENT DOCUMENTS

| | | | |
|---|---|---|---|
| 2,379,158 | 6/1945 | Kalischer | 73/61.4 X |
| 4,041,502 | 8/1977 | Williams et al. | 73/61.4 X |
| 4,118,974 | 10/1978 | Nozaki et al. | 73/61.4 |
| 4,194,391 | 3/1980 | Rosenberger | 73/61.4 |

FOREIGN PATENT DOCUMENTS 2614971 10/1977 Fed. Rep. of Germany ....... 73/61.4

Primary Examiner—Gerald Goldberg
Assistant Examiner—Joseph W. Roskos
Attorney, Agent, or Firm—Kenyon & Kenyon

[57] ABSTRACT

In a device for the automatic measurement of the settlable solids content of a liquid which includes a light transparent vertical measuring tube, a pump for filling the tube with a liquid and a photoelectric scanning head for finding the position of the boundary layer of the deposited solids, and means for emptying of the tube once it has been filled, the measurement of the settlable solids, which has taken place is facilitated by utilizing a piston within the measuring tube which is adapted to be displaced upward thereby permitting movement of the solids to a detector and easy removal of the liquid once the measurement has been made.

22 Claims, 11 Drawing Figures

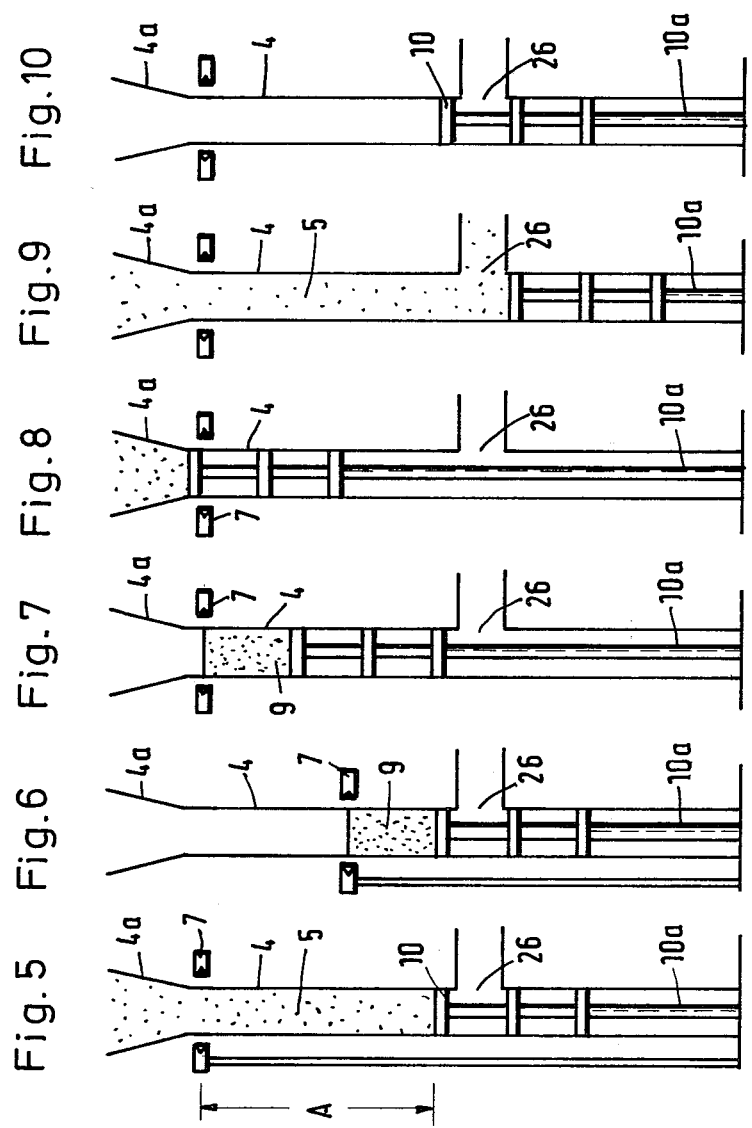

DEVICE FOR MEASURING THE SOLIDS CONTENT OF A LIQUID

BACKGROUND OF THE INVENTION

This invention relates to a device for the automatic measurement of the settlable solids content of a liquid, especially of a waste water/activated sludge mixture, with a light transparent vertical measuring tube which is filled with the liquid by a pump, and with a photoelectric scanning head for finding the position of the boundary layer of the deposited layer of solids (for instance, activated sludge).

Such a device is known from DE-OS No. 14 98 715. The design of this known device is expensive since at least two valves are required for proper functioning and also a cleaning device which must be run into the measuring tube to keep the inside wall of the measuring tube clean. The valves and the cleaning device require additional control means. In this known device, the liquid containing the solids is furthermore transported into the measuring tube by a pump which mixes, and thereby changes, the solids in the liquid. Also, the pump and the valves can be fouled by the solids contained in the liquid.

SUMMARY OF THE INVENTION

It is an object of the present invention to provide a device of the type mentioned at the outset, in which the design is less expensive, fewer control and/or regulating means are required and an additional cleaning device can be dispensed with. It is a further object of the present invention to decrease the trouble proneness and the maintenance required of a device of the type mentioned at the outset.

According to the invention, these problems are solved by the provision that a piston, by which the liquid contained in the measuring tube can be displaced upward, is arranged in the measuring tube.

The solution according to the present invention creates a device of the simplest possible design which requires no expensive additional cleaning device and has no valves. The device operates in an essentially trouble-free manner and has control and regulating means which can be built at a low cost. The measuring tube can have customary standardized dimensions, and a further lower closure of the measuring tube is not necessary since the piston constitutes the closure at the bottom.

Advantageous further embodiments of the invention are given in the subclaims.

Two embodiment examples of the invention are shown schematically in the drawings and will be described in detail in the following. There is shown in

BRIEF DESCRIPTION OF THE DRAWINGS

FIGS. 5 to 10 are enlarged sections from FIG. 4 in different operating positions.

DETAILED DESCRIPTION

Figure 1:
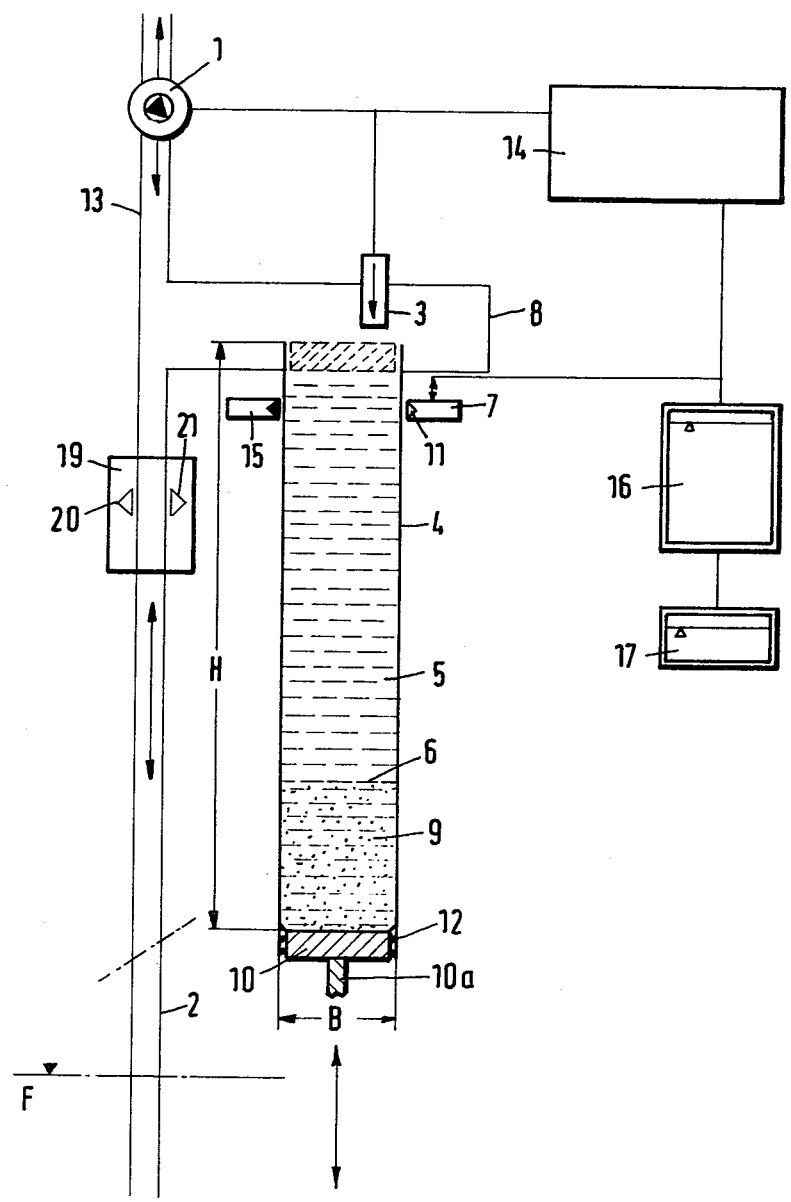
FIG. 1 is a vertical section through a first embodiment of the present invention.

A liquid feed and discharge line 2, which is arranged vertically or at least has a slope, has its lower opening extending into a liquid F at a point which serves as the sampling point and may be a channel between two basins of a water purification plant. The line 2 leads to the underside or the bottom of an overflow vessel 8, into the bottom of which a measuring tube 4 also leads (calibrated precision tube of glass with scale), the longitudinal axis of which is arranged vertically. The wall of the measuring tube 4 extends a few centimeters into the vessel 8 and the measuring tube is closed off at its underside by a piston 10 which can be moved up and down in the measuring tube pneumatically, hydraulically or via a linkage by a device, not shown. The height H and the width B of the measuring tube correspond to a standard tube or cuvette for measuring the solids content of a liquid.

From the top side of the overflow vessel 8, a line 13, which leads to a pump 1 which draws off air contained in the overflow vessel and is controlled by a control device 14 which also controls other parts of the device begins. The pump 1 does not come into contact with waste water, so that it cannot foul up and wear out rapidly. A switching device 3 extends into the overflow vessel 8 from above switching device 3 comprises an electrode and delivers a pulse to the control device 14 as soon as the liquid level in the overflow vessel reaches the electrode whereupon the pump 1 is switched off.

A scanning head 7 surrounding the measuring tube includes a light gate with a light source 11 and a photo cell 15. The scanning head 7 can be moved up and down along the measuring tube and is controlled by the connected control device 14 in such a manner that the scanning head 7 stops as soon as the light gate is interrupted by a layer of solids 9 (for instance, activated sludge) deposited in the measuring tube 4. Thereby, the scanning head 7 is stopped at the height of the top side 6 (boundary layer) of the layer of solids 9. The scanning head 7 is moved by a height adjustment device, not shown (for instance, a motor via a spindle, not shown), and the exact position of the scanning head 7 is indicated by a precision potentiometer on the output shaft. The position of the scanning head 7 and thereby, the height of the layer of solids 9 is transmitted to an indicating instrument 16, and these data are further entered into a memory 17. With this device, it is not only possible to automatically measure the deposited layer of solids after a given settling time (and this, quasi-continuously at short time intervals), but the settling rate can also be displayed by the indicating instrument 16.

At its circumference, the piston 10 has coaxial, ring-shaped elements 12 which consist of an elastic material, especially of rubber or plastic, and rest against the inside wall of the measuring tube 4, forming a seal. These elements fastened to the piston are constructed in such a manner that they clean the wall of the measuring tube during the motion of the piston 10.

The device is controlled by the control device 14 as follows:

By switching on the pump 1, air is drawn off from the overflow vessel 8 and liquid is thereby suctioned from the sampling point through the line 2 into the vessel 8. As soon as the liquid level in the vessel 8 has exceeded the upper edge of the measuring tube 4, the measuring tube is filled, and thereafter, the liquid level continues to rise until it has reached the electrode of the switching device 3. The signal generated by the liquid level is delivered by the switching device 3 to the control device 14 and causes the pump 1 to be switched off. Thereupon, the liquid contained in the vessel 8 flows back to the sampling point through the line 2 due to its weight, while air is flowing in through the stopped pump 1. If the design of the pump 1 does not allow air to flow through while it is standing still, or if the return of the liquid contained in vessel 8 is to be accelerated, the pump can also be switched on in such a manner that is pushes air into the vessel 8. The liquid 5 (for instance, the waste water) contained in the measuring tube 4 remains there for a given length of time, so that the solids contained in the liquid can settle. During the settling time, the scanning head 7 can follow the top side 6 of the layer of solids 9 which is displaced downward, and transmit to the indicating equipment 16 data which lead to the recording of a distance-time diagram. Alternatively, the scanning head 7 can also stand still for a given length of time and only then find the top side of the layer of solids 9, whereupon the distance traveled by the scanning head is transmitted to an indicating instrument.

After the measuring operation by the scanning head 7, the piston 10 is moved from its (up to then) lower position upward to the upper edge of the measuring tube, whereby the liquid contained in the measuring tube 4 is pushed into the overflow vessel 8 and runs off from the latter through the line 2. By moving the piston 10 up, the inside wall of the measuring tube is also cleaned. Thereupon, the piston returns into its lower position and the device is ready for a following operating cycle.

Prior to a new measuring cycle, the pump 1 generates and overpressure. Thereby, the solids/liquid mixture which had penetrated into the suction tube during the measuring period, is pushed out. This ensures that fresh measurement material gets into the measuring system for each measuring cycle.

Figure 2:
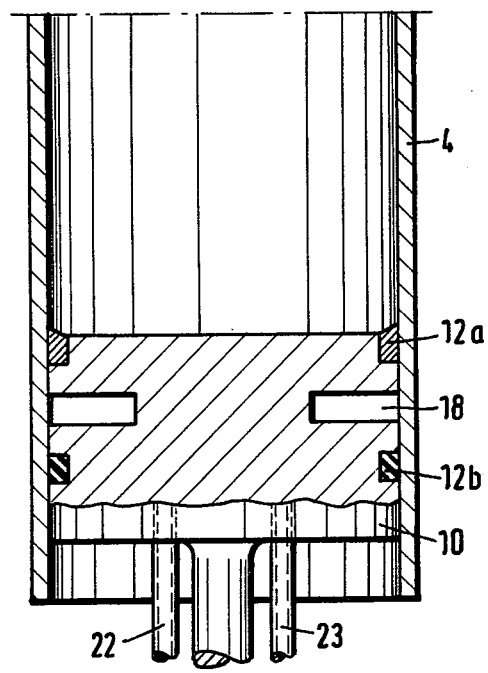
FIG. 2 is an enlarged vertical section through the piston according to FIG. 1 including a section of the measuring tube.
Figure 3:
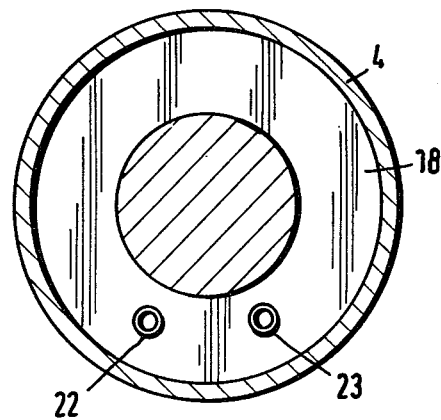
FIG. 3 is a horizontal section through the piston and the measuring tube according to FIGS. 1 and 2.

The piston shown in FIGS. 2 and 3 has, besides the wiper ring 12a and the sealing ring 12b, a groove 18 for receiving a cleaning and/or lubricating solution. The cleaning groove can be filled exclusively with solution or additionally, with a sponge-like material. The solution can be renewed manually (service intervals) or also automatically by means of a small intermittently operating hose pump via lines 22 and 23. A radiation or sound source 20 contained in a housing 19 is placed on the outside of the feed and discharge line 2 in a region which is radiation permeable or sound permeable. The sound waves or rays of the source 20 pentrate the liquid. Depending on the solids content in the liquid, more or fewer rays or sound waves arrive at a receiver 21 contained in the housing on the opposite side of the line 2, so that the density of the solid matter can be calculated and the weight of the solid material determined. A computer, not shown, is connected to the device of the present invention. The data representing the motion of the scanning head 7 over a fixed time interval and thereby, the settling behavior of the solid matter, is fed to the computer. Into this computer are further entered the position or height of the scanning head or the top side 6 of the layer of solids (volume of solids) and the density of the solid matter (weight) in the feed line 2. From these data, the computer calculates a single value or several values which give information regarding nitrification, denitrification and oxygen demand of the waste water.

While in the method described so far, the height of the top side (boundary layer) 6 [] of the layer of solids 9 was measured by the descent of the scanning head 7 to this top side, the piston 10 can also push the entire layer of solids 9 slowly upward until the top side 6 reaches the scanning head 7. The travel distance of the piston 10 and the piston rod fastened to the piston therefore indicates the position of the boundary layer 6. A drive mechanism 24 for the piston rod 10a (FIG. 4) arranged below the piston includes a double potentiometer which is driven indirectly or directly by the piston rod 10a and indicates the position of the piston 10. By exact control of the up and down movement and the stopping of the piston 10 at desired points, it is also possible to push a given portion or percentage of the liquid 5 contained in the measuring tube 4 out of the measuring tube 4 by raising the piston 10 and then running the piston 10 back into its lower position, so that an air space corresponding to the amount of water pushed out is generated in the measuring tube 4. Into this upper empty space of the measuring tube 4, dilution water can be fed through a line, which is not shown in FIGS. 1 to 3 and is designated with 25 in FIG. 4. Thus, the amount of water required for the dilution can be determined exactly and easily via the drive mechanism 24, not shown in FIG. 1.

Figure 4:
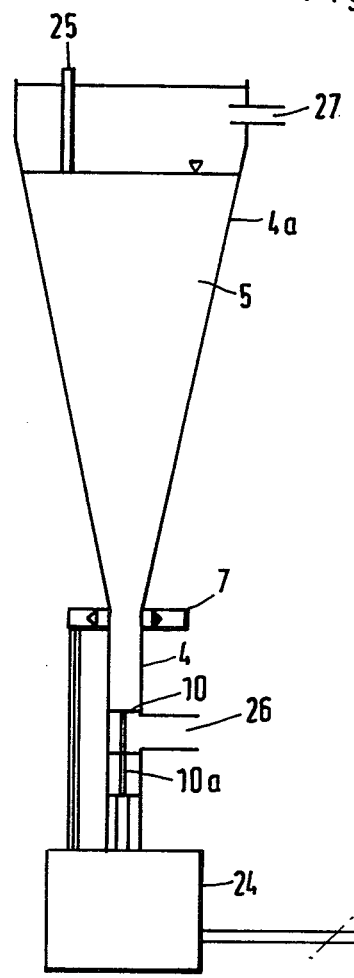
FIG. 4 is a vertical section through a second embodiment of the present invention.

As shown in FIG. 4, the measuring tube 4 can be extended downward beyond the position of the piston 10 shown in FIG. 1 (filling position) and in this extension of the measuring tube there is a lateral run-off opening 26 which, in the filling position of the piston 10, is separated by the piston from the rest of the measuring tube and is opened by moving the piston 10 down. Below the piston 10, further pistons 10' and 10" may be provided on the piston rod 10a in order to improve the guidance of the piston.

In the embodiment shown in FIGS. 4 to 10, the measuring tube 4 has in its upper portion a conical enlargement, the shape and dimensions of which correspond to a known sedimentation settler. This makes accurate measurement and working with conical settlers possible. In the vicinity of the upper edge of the conically expanded section, there is an opening 27 in the wall, which works as a run-off, inlet and/or overflow. In the upper portion of the expanded section 4a there is also the already mentioned line 25, the outlet opening of which is arranged tangentially to the outside wall of this expanded section, whereby mixing of dilution water with the contents of the measuring tube is improved. With the measuring tube empty, cleaning water can further be introduced which, due to the tangential outlet opening of the line 25, runs along the wall on an inside circle or helix and thereby cleans the inside wall of dirt particles quickly, thoroughly and with small amounts of water.

Figure 11:
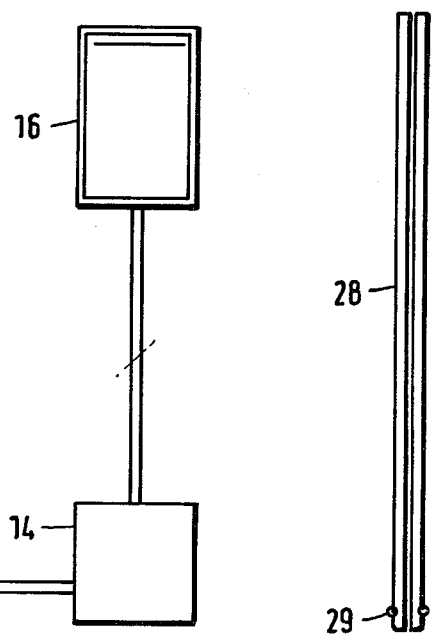
FIG. 11 is a plug for separating the layer of solids from the supernatant liquid.

In order to separate the layer of solids 9 from the supernatant liquid 5 for later investigations and measurements, the tube 28, which has a smaller outside diameter than the inside diameter of the measuring tube 4 and is shown in FIG. 11, can be inserted into the measuring tube 4 from above. In the region of the lower end, the tube 28 has on the outside a sealing ring 29 which rests tightly against the inside wall of the measuring tube 4. If this tube 28, which acts with its lower side as a plug, is inserted into the measuring tube 4 far enough that the underside of the tube 28 rests approximately on the upper side 6 of the layer of solids 9, then the liquid 5 in the measuring tube 4 is displaced upward through the interior of the tube 28. Thereupon, the upper opening of the tube 28 is closed off by a valve, not shown, or a finger and the layer of solids 9 can be drained off through the outlet opening 26 by lowering the piston 10. The tube 28 is made to follow while the piston 10 is lowered.

In FIGS. 5 to 10, the operation of the device shown in FIG. 4 is shown schematically. With the outlet opening 26 closed off by the piston 10, water containing settlable matter is filled from above into the measuring tube 4 and the conically expanded portion 4a of the measuring tube. After a given time interval, a layer of solids 9 has formed. The height of the top side of this layer of solids is measured by lowering the scanning head 7, as is shown in FIG. 6, or the layer of solids 9 is slowly brought to the scanning head 7 (FIG. 7) and the travel distance of the piston 10 and the piston rod 10a indirectly furnishes the measurement value; the travel of the piston and the piston rod must be subtracted from the distance A between the surface of the piston and the scanning head 7.

After the height of the layer of solids 9 has been measured, the inside wall of the measuring tube 4 is cleaned by repeated raising and lowering of the piston 10 and then the piston is lowered far enough that the run-off opening 26 is open (FIG. 9) and the layer of solids 9 and the liquid 5 can run off. Thereupon, clean water or a cleaning fluid is admitted through the line 25 for cleaning the inside wall of the measuring tube 4 and the expanded section 4a. The piston 10 is then moved again into its starting position, closing the run-off opening 26 (FIG. 10).

I claim:

1. In a device for the automatic measurement of the settlable solids content of a liquid including a light transparent vertical measuring tube, a pump for filling said measuring tube with the liquid, and a photoelectric scanning head for finding the position of the boundary layer of the deposited solids, the improvement comprising a piston disposed in said measuring tube and adapted to displace said liquid contained in said measuring tube upward.

2. The improvement according to claim 1, wherein said scanning head is fixed and wherein said boundary layer is adapted to be moved to said scanning head by said piston.

3. The improvement according to claim 1, wherein said scanning head is adapted for movement along said measuring tube so as to be moved to said boundary layer.

4. The improvement according to claim 1, and further including ring-shaped elements for cleaning the inside wall of said measuring tube fastened to the circumference of said piston.

5. The improvement according to claim 1, wherein said piston forms a liquid-tight closure for said measuring tube when in its lower position.

6. The improvement according to claim 1, and further including a storage of overflow vessel into which the upper opening of said measuring tube leads.

7. The improvement according to claim 6, wherein said pump comprises an air pump connected to the top side of said overflow vessel for evacuating air from said vessel and further including a liquid feed line opening into the under side of said vessel.

8. The improvement according to claim 7, wherein said liquid feed line is also adapted to act as a discharge line.

9. The improvement according to claim 6, and further including a switching device disposed in said overflow vessel, said switching device controlled by the liquid level therein and adapted to turn off said pump after a given filling level is reached.

10. The improvement according to claim 1, wherein said piston has a circular slot formed in the circumference between the top and bottom sides thereof and means for supplying a cleaning and/or lubricating liquid to said circular slot.

11. The improvement according to claim 8, and further including means having a sound or radiation source for penetrating the liquid, disposed at said feed line, for measuring the density of the solids in said liquid.

12. The improvement according to claim 11, and further including a computer receiving as data inputs: the motion of the scanning head during a given time interval; the position of the scanning head at the end of the set measuring time; and the densities of the solids contained temporarily in said feed line, said computer adapted to calculate at least one value from these measurement results.

13. The improvement according to claim 1, and further including a run-off opening in said measuring tube at a point located below the measuring range in which the piston is located when said measuring tube is being filled with liquid.

14. The improvement according to claim 13, and further including an extension of said measuring tube below said run-off opening into which said piston can be moved.

15. The improvement according to claim 14, wherein said measuring tube is conically flared towards its top above a cylindrical measuring range.

16. The improvement according to claim 15, wherein said run-off opening is disposed in the wall of said measuring tube in the vicinity of the upper edge of said conically expanded portion.

17. The improvement according to claim 15, and further including a tangential inlet opening for dilution of water and/or cleaning water disposed in the vicinity of the upper edge of said conically expanded portion.

18. The improvement according to claim 15, and further including a plug for separating the lower cylindrical range of said measuring tube from the upper conical range in a liquid-tight manner, said plug adapted to be brought into the conical range.

19. The improvement according to claim 18, wherein said plug is formed by or supported by the lower portion of said tube.

20. The improvement according to claim 19, wherein said plug includes a sealing ring at its outside.

21. A method for the automatic measurement of the settlable solid content in a liquid, utilizing a device which includes: a light transparent vertical measuring tube; a pump for filling said measuring tube with the liquid; a photoelectric scanning head for finding the position of the boundary layer of the deposited solid; a piston disposed in said measuring tube; an overflow vessel into which the upper end of said measuring tube extends; and a switching device controlled by the liquid level for controlling said pump, comprising:

a. first drawing liquid into the overflow vessel by evacuating air from the overflow vessel with said pump, said liquid thereby running from said overflow vessel into said measuring tube, until said measuring tube is filled, with said piston disposed at the bottom thereof;

b. continuing to draw liquid into said overflow vessel until said switching device switches said pump off thereby permitting liquid in the overflow vessel to run out;

c. after a settling time, ascertaining the height of the layer of solids in said tube with said photoelectric scanning head and transmitting said level to a connected measuring device; and d. then raising said piston to displace the liquid in said measuring tube into said overflow vessel from which it runs off.

22. A method according to claim 21, wherein said step of ascertaining comprises moving the contents in said measuring tube upward with said piston until the boundary of said layer of solids reaches said scanning head.

* * * * *